United States Patent
Schulz et al.

(10) Patent No.: US 10,792,583 B2
(45) Date of Patent: Oct. 6, 2020

(54) PROCESS AND APPARATUS FOR CONTROLLING THE SPLIT OF LIQUID REFLUX IN A DIVIDED WALL COLUMN

(71) Applicant: UOP LLC, Des Plaines, IL (US)

(72) Inventors: Russell C. Schulz, Glen Ellyn, IL (US); Chad A. Williams, Arlington Heights, IL (US); James W. Harris, Palatine, IL (US); Nikunj Manubhai Patel, Melrose Park, IL (US)

(73) Assignee: UOP LLC, Des Plains, IL (US)

(*) Notice: Subject to any disclaimer, the term of this patent is extended or adjusted under 35 U.S.C. 154(b) by 0 days.

(21) Appl. No.: 16/368,310

(22) Filed: Mar. 28, 2019

(65) Prior Publication Data

US 2019/0299116 A1 Oct. 3, 2019

Related U.S. Application Data

(60) Provisional application No. 62/650,170, filed on Mar. 29, 2018.

(51) Int. Cl.
| | | |
|---|---|---|
| *B01D 3/14* | (2006.01) | |
| *B01D 3/42* | (2006.01) | |
| *C07C 39/04* | (2006.01) | |
| *C07C 37/74* | (2006.01) | |
| *C07C 37/52* | (2006.01) | |

(52) U.S. Cl.
CPC ........... *B01D 3/141* (2013.01); *B01D 3/4233* (2013.01); *C07C 37/74* (2013.01); *C07C 39/04* (2013.01); *B01D 2257/7027* (2013.01); *C07C 37/52* (2013.01)

(58) Field of Classification Search
CPC ...... B01D 3/141; B01D 3/4233; C07C 37/74; C07C 39/04
See application file for complete search history.

(56) References Cited

U.S. PATENT DOCUMENTS

| | | | | |
|---|---|---|---|---|
| 3,412,016 A | * | 11/1968 | Graven | C10G 31/00 208/354 |
| 4,230,533 A | * | 10/1980 | Giroux | B01D 3/4255 203/1 |
| 7,129,387 B2 | * | 10/2006 | Reyneke | B01D 3/14 585/809 |
| 9,815,756 B2 | | 11/2017 | Schmidt et al. | |
| 10,399,004 B2 | * | 9/2019 | Hoyme | C07C 45/84 |
| 2002/0068840 A1 | * | 6/2002 | Weber | C07C 37/74 568/385 |
| 2005/0034970 A1 | | 2/2005 | Schwarz et al. | |

FOREIGN PATENT DOCUMENTS

| | | |
|---|---|---|
| CN | 107501093 A | 12/2017 |
| CN | 107837552 A | 3/2018 |

OTHER PUBLICATIONS

International Search Report from corresponding PCT application No. PCT/US2019/024829, dated Jul. 11, 2019.
Written Opinion from corresponding PCT Application No. PCT/US2019/024829, dated Jul. 8, 2019.

* cited by examiner

*Primary Examiner* — Jonathan Miller

(57) ABSTRACT

The present invention relates to the fractionation technology that is used to create purified phenol and acetone products. More specifically, the present invention relates to a fractionation technology that is used to create crude acetone and crude phenol streams using a dividing wall column intended to remove cumene, alpha-methyl styrene and water from the product side of the wall.

12 Claims, 2 Drawing Sheets

PROCESS AND APPARATUS FOR CONTROLLING THE SPLIT OF LIQUID REFLUX IN A DIVIDED WALL COLUMN

RELATED APPLICATIONS

This application claims the benefit of U.S. Provisional Patent Application Ser. No. 62/650,170 filed on Mar. 29, 2018, the entirety of which is incorporated herein by reference.

FIELD

The present invention relates to the fractionation technology that is used to create a purified phenol product. More specifically, the present invention relates to a fractionation technology that is used to create crude acetone and crude phenol streams using a dividing wall column intended to remove cumene, alpha-methyl styrene and water from the product side of the wall.

BACKGROUND

Phenol is manufactured via air oxidation of cumene to cumene hydroperoxide (CHP), followed by acid-catalyzed cleavage of the latter to phenol and acetone, and known as CHP decomposition. CHP decomposition is a very exothermic reaction which is normally carried out on a commercial scale in continuous stirred or back-mixed reactors. In such reactors only a small fraction of CHP is unreacted at any given time and the reaction medium consists essentially of the products of decomposition of CHP, i.e., phenol and acetone, plus any solvent (e.g., cumene) and other materials added with CHP to the reactor. During cumene oxidation small amounts of dimethyl phenyl carbinol (DMPC) and acetophenone are also formed. In the presence of acid catalyst, DMPC dehydrates to alphamethylstyrene (AMS), a useful by-product. These components, along with other byproducts, comprise the bulk of the fractionation feed.

The traditional design of phenol fractionation flow scheme includes two columns that are used to separate the acetone, cumene, and AMS in the fractionation feed from the phenol. Acetone and a portion of the cumene and water are first distilled to the overheads of the crude acetone column (first column), which operates at slightly above the atmospheric pressure. Acids in the overhead streams would lead to fouling in the subsequent system. The bottoms, containing the remainder of the cumene and water and the bulk of formic acid and acetic acid, along with essentially all of the AMS, phenol and higher-boiling by-products are routed to the cumene-AMS column (second column), which operates at fairly deep vacuum, in which the remaining water and cumene, along with the bulk of the AMS and acids are distilled to the overheads. The water phase separates from the organic phase in the cumene-AMS column overhead receiver to form a net overhead aqueous stream comprising almost all of the water. The bulk of the acids and some phenol partition to the aqueous phase. The organic phase stream from the receiver comprises mainly cumene and AMS. However, the organic stream also contains a significant amount of phenol, due to the low-boiling azeotrope formed by phenol and AMS, and some organic acids, due to partitioning with the aqueous phase. The net bottoms stream from the cumene-AMS column comprises trace amounts of AMS, the bulk of the phenol, impurities that distill with phenol, and higher-boiling impurities and residue. The net bottoms stream goes to a downstream system in which impurities are removed via chemical reaction and distillation to produce a high-purity phenol product and also a residue stream.

The use of such multiple column systems for the initial phenol fractionation results in high capital equipment costs and operating costs. The conventional design of single distillation column known in the prior art do not provide high recovery of acetone to the overhead steam. Excessive acetone in the net side draw aqueous stream and net side draw organic stream require additional processing to remove the excess acetone and/or loss of the acetone and/or increased costs for disposal or further processing of the streams containing the excessive acetone. There is a need for a new process and apparatus to efficiently operate the phenol unit with significant reduction in the capital and operating costs. Also, there is a need for an improved and more economical process and simplified apparatus design for the phenol fractionation that can improve the yield of phenol and acetone.

SUMMARY

The present disclosure describes improvements to the distillation column system described in U.S. Pat. No. 9,815,756, "Methods and apparatuses for phenol fractionation in a single dividing wall column" and other distillation column systems for which two liquid phases form in the liquid immediately above the dividing wall, or could form at that point. That liquid forms the reflux streams for the two sides of the column that are separated by the dividing wall. Design and operation of a dividing wall column requires that the reflux stream be apportioned to the two sides of the dividing wall. When the liquid reflux forms two liquid phases, potential problems that could arise from splitting a single total liquid reflux stream comprising both liquid phases from above the dividing wall into two liquid steams to apportion the reflux to each side of the dividing wall include the following:

Were it not for the aqueous phase in the reflux, there would be no aqueous phase liquid on the feed side of the dividing wall: Simulation shows the aqueous phase from the reflux disappearing so that only organic phase liquid appears there. In actual operation with reflux comprising two liquid phases, due to less than 100% efficiency for actual trays or packing, some aqueous phase will certainly exist at the liquid reflux inlet to the top of the feed side, and might persist beyond that point. Within a short distance of entering the feed side, sufficient water will be distilled out of the liquid phase, so that the bulk of the aqueous phase will disappear, so that the liquid will consist of nearly all organic phase, with some water in solution. However, the aqueous phase reflux contains significant concentrations of compounds that are significantly more soluble in the aqueous phase than in the organic phase, such as formic acid. As the amount of aqueous phase decreases, the concentration of formic acid would increase, resulting in a more corrosive environment. Compounds that are soluble in the aqueous phase but insoluble in the organic phase, such as salts of formic acid, will tend to form solid precipitate particles when the aqueous phase disappears, potentially causing fouling of the trays or packing.

Due to the different physical properties of the two liquid phases, the apparatus used to split the reflux stream will not necessarily produce streams containing the same proportions of each phase. That can result in undesirable effects on the distillation performance of the column. For example, in splitting the flow of a liquid stream containing a mixture of liquid organic phase and liquid aqueous phase, if the apparatus used produces a liquid reflux stream to the feed side containing proportionally more aqueous phase, then, because the columns operation requires that aqueous phase net product leave the column through the product line outlet on the product side, with the total rate of reflux to the product side maintained so as to achieve the required distillation, mass, and energy balance requirements for the product side, the flow rates and compositions must change so that the reflux rate and composition to the product side are essentially the same as they would be with a uniform split of the reflux phases to each side of the dividing wall. However, with reboiler heat input held constant, and a greater than proportional flow of aqueous phase splitting to the feed side, to satisfy the internal distillation mass and energy balances the rate of total aqueous phase reflux above the dividing wall must increase, thus the rate of total organic reflux above the dividing wall must decrease, and the rate of organic phase reflux to the feed side must also decrease. As described above, were it not for the aqueous phase reflux, there would not be an aqueous phase in the liquid on the feed side. As such, the aqueous phase reflux is less effective for distillation on the feed side, and increasing the aqueous reflux at the expense of organic reflux either results in poorer distillation separation on the feed side, or requires increasing the reflux rate to the feed side, thus the total reflux rate, thus reboiler heat input, in order to achieve the same distillation separation.

This invention greatly alleviates these problems by separating the two liquid phases of the reflux from above the dividing wall and controlling the flow of each phase to each of the two sides of the dividing wall.

A first embodiment is a process comprising a dividing wall column having a feed side and a product side, wherein the feed side comprises a feed line inlet and wherein the product side comprises a product line outlet; wherein the liquid reflux immediately above a dividing wall forms or could form two liquid phases, wherein the two liquid phases of the reflux stream are, by any means, separated wherein the liquid phase reflux stream comprising primarily one of the liquid phases is directed in its entirety to the product side of the dividing wall, and the liquid phase reflux stream comprising primarily the other liquid phase is split into two streams, with one of those streams directed as reflux to the product side and the other of those streams is directed as reflux to the feed side, wherein for the phase stream that is split the flow apportioned to the product side versus the feed side is controlled.

A second embodiment is an apparatus, comprising a dividing wall column having a feed side and a product side, wherein the feed side comprises a feed line inlet and wherein the product side comprises a product line outlet; wherein the liquid reflux immediately above a dividing wall forms or could form two liquid phases; wherein a decanter is positioned above a partition of the dividing wall column to effect separation of the two liquid phases of the reflux stream wherein the liquid phase reflux stream from the decanter comprising primarily one of the liquid phases is directed in its entirety to the product side of the dividing wall, and the liquid phase reflux stream from the decanter comprising primarily the other liquid phase is split into two streams, with one portion of each directed as reflux to the product side and the other portion to the feed side, wherein for the phase stream that is split the flow apportioned to the product side versus the feed side is controlled.

A third embodiment of the invention is a system for controlling the reflux flows in a dividing wall column, comprising a dividing wall having a feed side and a product side, a decanter, a liquid-liquid phase interface level controller, a liquid level controller, a flow indicator, a first flow controller with associated flow control valve, a second flow controller with associated flow control valve, and a third flow controller with associated flow control valve, a ratio controller, and a control signal summing device.

A fourth embodiment is a process, comprising a dividing wall column having a feed side and a product side, wherein the feed side comprises a feed line inlet and wherein the product side comprises a product line outlet; wherein the liquid reflux immediately above a dividing wall forms or could form two liquid phases, wherein the two liquid phases of the reflux stream are separated wherein each liquid phase reflux stream is split into two streams, with one portion of each directed as reflux to the feed side and the other portion to the product side, wherein for each phase the flow apportioned to the feed side versus the product side is controlled; wherein the apportionment of the two liquid phases can be the same or different, and the apportionment can be entirely to either the feed side or the product side, within the constraints of the reflux requirements.

A fifth embodiment is an apparatus, comprising a dividing wall column having a feed side and a product side, wherein the feed side comprises a feed line inlet and wherein the product side comprises a product line outlet; wherein the liquid reflux immediately above a dividing wall forms or could form two liquid phases; wherein a decanter is positioned above a partition of the dividing wall column to effect separation of the two liquid phases of the reflux stream wherein each liquid phase stream from the decanter is split into two streams, with one portion of each directed as reflux to the feed side and the other portion to the product side, wherein for each phase the flow apportioned to the feed side versus the product side is controlled; wherein the apportionment of the two liquid phases can be the same or different, and the apportionment can be entirely to either the feed side or the product side, within the constraints of the reflux requirements.

A sixth embodiment of the invention is a system for controlling the reflux flows in a dividing wall column, comprising a dividing wall column having a feed side, a product side, a decanter, a liquid-liquid phase interface level controller, a liquid level controller, a first flow indicator, a second flow indicator, a first flow controller with associated flow control valve, a second flow controller with associated flow control valve, a third flow controller with associated flow control valve, and a fourth flow controller with associated flow control valve, a first ratio controller, a second ratio controller, and a control signal summing device.

In the foregoing, all temperatures are set forth in degrees Celsius and, all parts and percentages are by weight, unless otherwise indicated. Other objects, advantages and applications of the present invention will become apparent to those skilled in the art from the following detailed description and drawings. Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

Definitions

As used herein, the term "stream", "feed", "product", "part" or "portion" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

Hydrocarbon molecules may be abbreviated C1, C2, C3, Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8, An where "n" represents the number of carbon atoms in the one or more aromatic molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three or more carbon atoms.

As used herein, the term "zone" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

As used herein, the term "primarily" means greater than 50% of the total stream to which it refers, or greater than 55%, or greater than 60%, or greater than 65%, or greater than 70%, or greater than 75%, or greater than 80%, or greater than 85%, or greater than 90%, or greater than 95%, or greater than 97%, or greater than 99%.

DETAILED DESCRIPTION

The following detailed description is merely exemplary in nature and is not intended to limit the application and uses of the embodiment described. Furthermore, there is no intention to be bound by any theory presented in the preceding background or the following detailed description.

Figure 1:
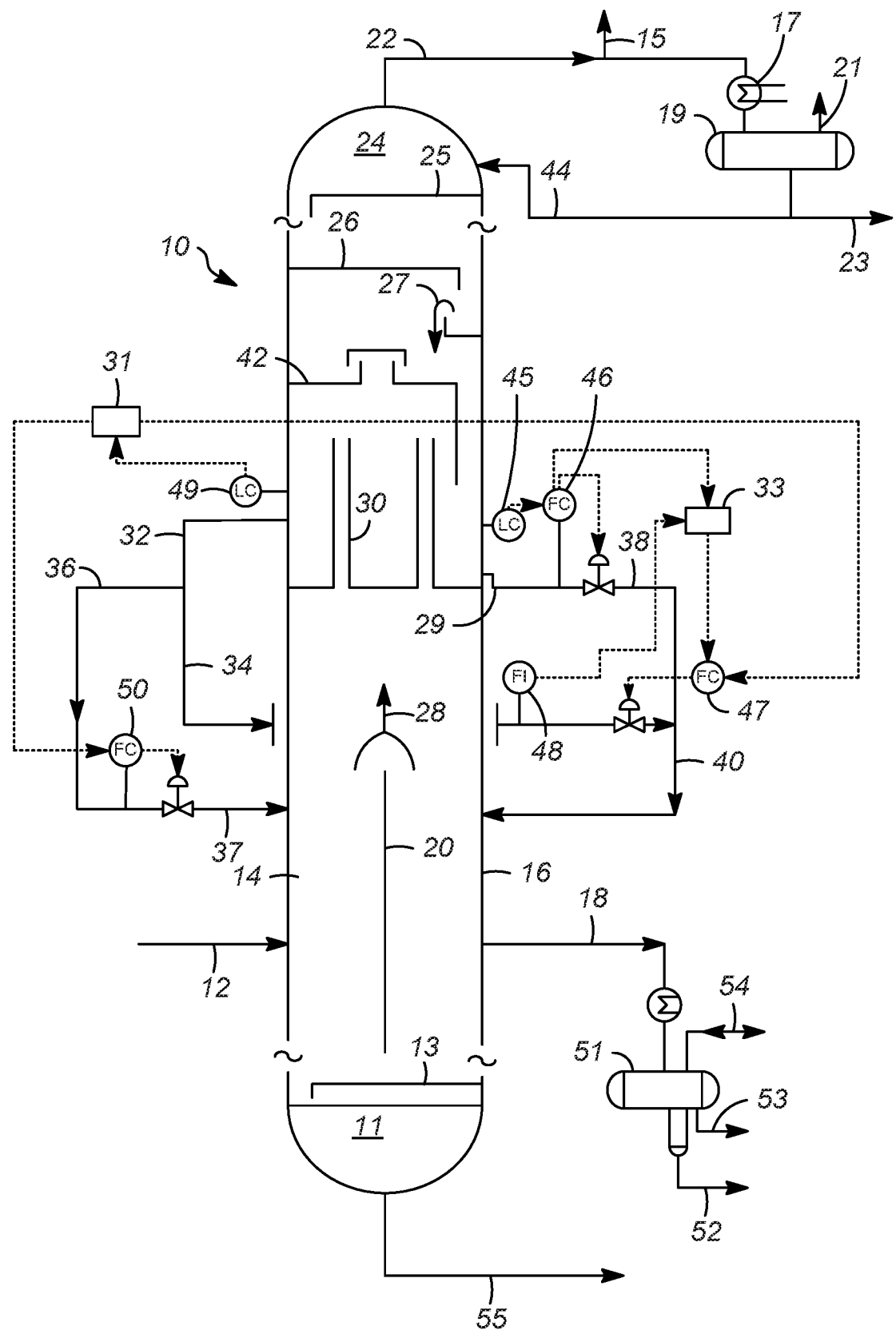
FIG. 1 illustrates one embodiment of a dividing wall column system of the present invention.

The description of the apparatus of this invention is presented with reference to the attached drawings. FIG. 1 illustrates a dividing wall column system intended to, by means of an internal decanter, separate the two liquid phases of the reflux from above the dividing wall, control both the liquid-liquid interface level and the overall liquid level in the decanter, send all of the liquid phase having higher density to the product side of the dividing wall as reflux, and adjust the ratio of the flow of the phase having lower density as the reflux to each of the two sides of the dividing wall.

FIG. 1 is a simplified diagram of the preferred embodiment of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

The various embodiments described herein relate to a dividing wall column intended to remove a product stream comprising a mixture of two liquid phases from the product side of the wall. As shown in FIG. 1, a dividing wall column 10 comprises a dividing wall 20 which separates a feed side 14 and a product side 16. A dividing wall column also typically comprises a bottom section 11, comprising a net liquid outlet 55, a reboiler system, and optionally one or more bottom-section active tray(s) 13 or packing. A dividing wall column typically also comprises a top section 24, with combined vapor 28 from the feed and product sides of the dividing wall flowing upward into the top section, and with a vapor outlet 22. A portion of the top overhead vapor from top vapor outlet 22 can optionally go to a net overhead vapor product 15. The remaining top overhead vapor goes to a condenser 17 in which the vapor is partially or totally condensed. The outlet from the condenser typically goes to an overhead receiver vessel 19. If the overhead vapor entering the condenser was not totally condensed, the remaining vapor typically leaves the top of the overhead receiver through vapor vent 21. A portion of the liquid from the receiver can optionally go to an overhead liquid stream 23. The remainder of the overhead liquid is returned to top section 24 as reflux via reflux inlet 44. Top section 24 typically comprises one or more upper-section active distillation trays 25 or packing; however, an alternate configuration without such upper-section active distillation tray(s) or packing is described elsewhere in this document. The feed stream 12 enters the dividing wall column 10 on the feed side 14. The column operates with compositions, conditions and rates such that liquid reflux stream 27 from first active distillation tray 26 above dividing wall 20 forms two liquid phases. The compositions, conditions and rates are such that liquid side draw product stream 18 withdrawn from the product side forms two liquid phases. In a typical configuration, liquid side draw product stream 18 flows to a settler 51, either with or without cooling, in which higher-density aqueous liquid stream 52 separates and is withdrawn separately from lower-density organic phase net product stream 53. Pressure equalization line 54 allows gas or vapor to enter or leave the settler 51 so the settler 51 can also serve as surge volume to facilitate more uniform flow of organic phase net product stream 53.

In a typical dividing wall column, in which the liquid reflux does not form two liquid phases (not shown), the reflux from the tray above the dividing wall is apportioned so that a part of the reflux is directed to each side of the dividing wall. When the liquid reflux forms two liquid phases, potential problems that could arise from splitting a single total liquid reflux stream comprising both liquid phases from above the dividing wall into two liquid steams to apportion the reflux to each side of the dividing wall include the following:

Were it not for the aqueous phase in the reflux, there would be no aqueous phase liquid on the feed side of the dividing wall: Simulation shows the aqueous phase from the reflux disappearing so that only organic phase liquid appears there. In actual operation with reflux comprising two liquid phases, due to less than 100% efficiency for actual trays or packing, some aqueous phase will certainly exist at the liquid reflux inlet to the top of the feed side, and might persist beyond that point. Within a short distance of entering the feed side, sufficient water will be distilled out of the liquid phase, so that the bulk of the aqueous phase will disappear, so that the liquid will consist of nearly all organic phase, with some water in solution. However, the aqueous phase reflux contains significant concentrations of compounds that are significantly more soluble in the aqueous phase than in the organic phase, such as formic acid. As the amount of aqueous phase decreases, the concentration of formic acid would increase, resulting in a more corrosive environment. Compounds that are soluble in the aqueous phase but insoluble in the organic phase, such as salts of formic acid, will tend to form solid precipitate particles when the aqueous phase disappears, potentially causing fouling of the trays or packing.

Due to the different physical properties of the two liquid phases, the apparatus used to split the reflux stream will not necessarily produce streams containing the same proportions of each phase. That can result in undesirable effects on the distillation performance of the column. For example, in splitting the flow of liquid reflux stream containing a mixture of liquid organic phase and liquid aqueous phase, if the apparatus used produces a liquid phase reflux stream to the feed side containing proportionally more aqueous phase, then, because the columns operation requires that aqueous phase net product stream leave the column through product line outlet for liquid side draw stream on the product side, with the total rate of reflux stream to the product side maintained so as to achieve the required distillation, mass, and energy balance requirements for the product side, the flow rate and composition of reflux stream from above the dividing wall must change so that the reflux stream rate and composition to the product side are essentially the same as they would be with a uniform split of the reflux phases to each side of the dividing wall. However, with reboiler heat input held constant, and a greater than proportional flow of aqueous phase splitting to the feed side reflux stream, to satisfy the internal distillation mass and energy balances, the rate of total aqueous phase reflux above the dividing wall must increase. Thus, the rate of total organic reflux above the dividing wall must decrease, and the rate of organic phase reflux in feed side reflux stream must also decrease. As described above, were it not for the aqueous phase reflux, there would not be an aqueous phase in the liquid on the feed side. As such, the aqueous phase reflux is less effective for distillation on the feed side, and increasing the aqueous reflux at the expense of organic reflux either results in poorer distillation separation on the feed side, or requires increasing the reflux rate to the feed side, thus the total reflux rate, thus reboiler heat input, in order to achieve the same distillation separation.

This invention greatly alleviates these problems by separating the two liquid phases of reflux stream 27 from above the dividing wall into two streams, a reflux stream 32 containing primarily the organic phase, and a reflux stream 29 containing primarily the aqueous phase, and controlling the split of each of those two streams to each side of the dividing wall. The aqueous reflux outlet for reflux stream 29 would typically be located slightly above the bottom of the separator, such as decanter 30, in the aqueous layer below the organic/aqueous interface 45. The organic reflux outlet for reflux stream 32 would typically be located above the organic/aqueous interface 45 but below the liquid level controller 49. There can be vapor chimneys extending to above the liquid level controller 49. By the terms "aqueous reflux outlet," "organic reflux outlet," "aqueous reflux inlet," and "organic reflux inlet," we mean that the aqueous reflux and organic reflux flow from the respective outlet or to the respective inlet. The positions described for the outlets from the separator or decanter refer to the positions relative to the liquid in the separator or decanter, without regard to the positions of the external connections. The outlet can be connected to the associated inlet on the outside of the dividing wall column, or there can be internal channels or piping connecting the outlet and inlet.

A first embodiment is a process, comprising dividing wall column 10 having feed side 14 and a product side 16, wherein the feed side comprises an inlet for feed stream 12 and wherein the product side comprises a product line outlet for liquid side draw stream 18; wherein the liquid reflux stream 27 from the first active distillation tray 26 above dividing wall 20 forms or could form two liquid phases, wherein the two liquid phases of the reflux stream are, by any means, separated wherein reflux stream 29 comprising primarily the aqueous phase is directed in its entirety to the product side of the dividing wall, and reflux stream 32 comprising primarily the organic phase is split into stream 34 and 36, with stream 34 directed as reflux to the product side and stream 36 directed as reflux to the feed side, wherein for the phase stream that is split the flow apportioned to the product side versus the feed side is controlled.

A second embodiment is an apparatus, comprising dividing wall column 10 having feed side 14 and a product side 16, wherein the feed side comprises an inlet for feed stream 12 and wherein the product side comprises a product line outlet for liquid side draw stream 18; wherein the liquid reflux stream 27 from the first active distillation tray 26 above dividing wall 20 forms or could form two liquid phases, wherein decanter 30 with optional collector tray 42, is positioned above dividing wall 20 of the dividing wall column to effect separation of the two liquid phases of reflux stream 27, wherein reflux stream 29 comprising primarily the aqueous phase is directed in its entirety to product side 16 of the dividing wall, and reflux stream 32 comprising primarily the organic phase is split into stream 34 and 36, with stream 34 directed as reflux to the product side and stream 36 directed as reflux to the feed side, wherein for the phase stream that is split the flow apportioned to the product side versus the feed side is controlled. There is no functional requirement for the reflux outlets from internal decanter 30 to have any particular orientation relative to the feed side or product side of the dividing wall.

A third embodiment of the invention is a system for controlling the reflux flows in a dividing wall column 10, comprising a dividing wall 20 having a feed side 14 and a product side 16, a decanter 30 with optional collector tray 42, a liquid-liquid phase interface level controller 45, a liquid level controller 49, a flow indicator 48, a first flow controller 46 with associated flow control valve, a second flow controller 47 with associated flow control valve, and a third flow controller 50 with associated flow control valve, a ratio controller 31, and a control signal summing device 33. There is no functional requirement for the reflux outlets from internal decanter 30 to have any particular orientation relative to the feed side or product side of the dividing wall.

Figure 2:
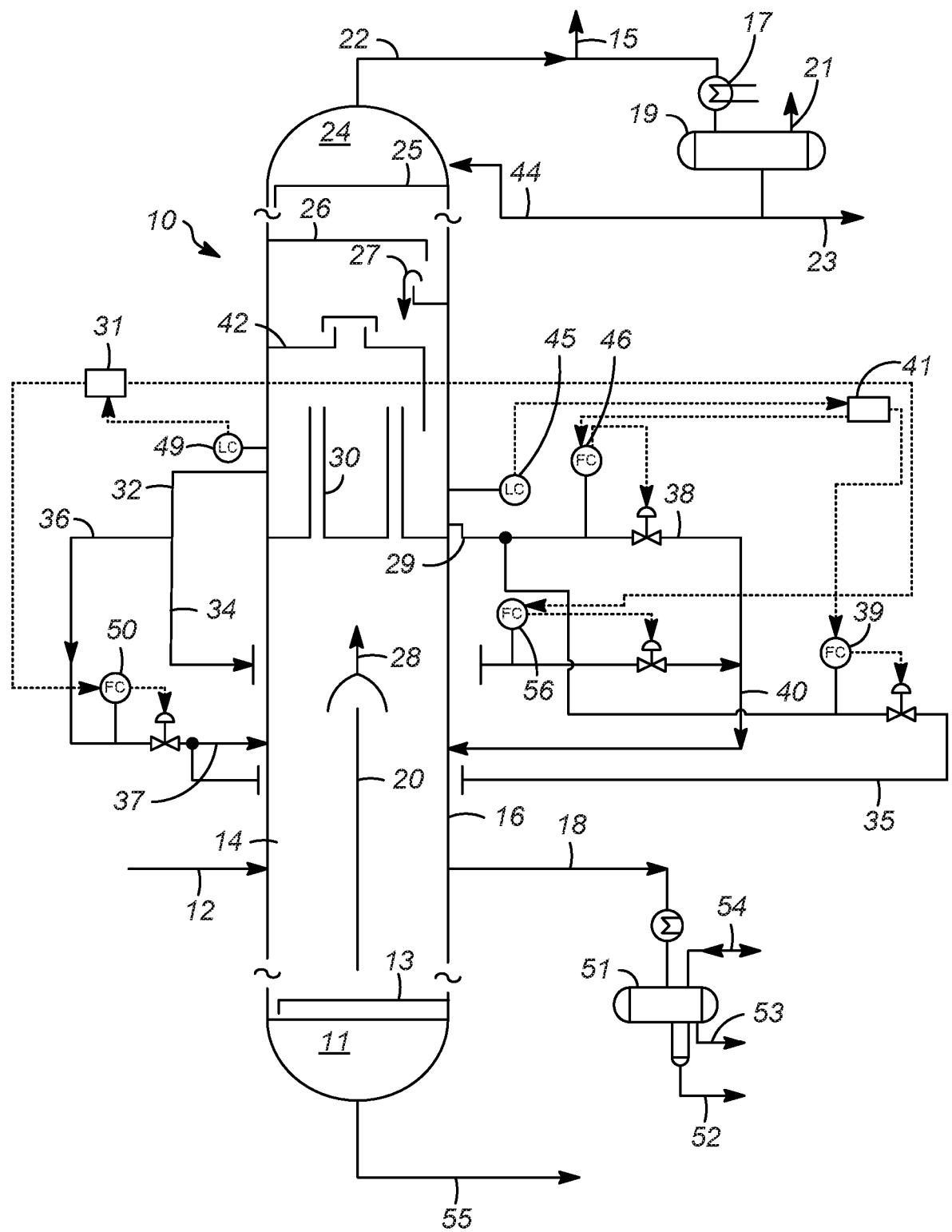
FIG. 2 illustrates another embodiment of a dividing wall column system of the present invention.

For the fourth, fifth, and sixth embodiments, refer to FIG. 2.

A fourth embodiment is a process, comprising dividing wall column 10 having feed side 14 and a product side 16, wherein the feed side comprises an inlet for feed stream 12 and wherein the product side comprises a product line outlet for liquid side draw stream 18; wherein the liquid reflux stream 27 from the first active distillation tray 26 above dividing wall 20 forms or could form two liquid phases, wherein the two liquid phases of the reflux stream are, by any means, separated wherein reflux stream 29 comprising primarily the aqueous phase is split into stream 38 and 35, with stream 38 directed as reflux to the product side and stream 35 directed as reflux to the feed side of the dividing wall 20, and reflux stream 32 comprising primarily the organic phase is split into stream 34 and 36, with stream 34 directed as reflux to the product side and stream 36 directed as reflux to the feed side, wherein for both of the phases the flow apportioned to the product side versus the feed side is controlled.

A fifth embodiment is an apparatus, comprising dividing wall column 10 having feed side 14 and a product side 16, wherein the feed side comprises an inlet for liquid side draw stream 12 and wherein the product side comprises a product line outlet for liquid side draw stream 18; wherein the liquid reflux stream 27 from first active distillation tray 26 above dividing wall 20 forms or could form two liquid phases, wherein decanter 30 with optional collector tray 42 is positioned above dividing wall 20 of the dividing wall column to effect separation of the two liquid phases of reflux stream 27, wherein reflux stream 29 comprising primarily the aqueous phase is split into stream 38 and 35, with stream 38 directed as reflux to the product side and stream 35 directed as reflux to the feed side of the dividing wall, and reflux stream 32 comprising primarily the organic phase is split into stream 34 and 36, with stream 34 directed as reflux to the product side and stream 36 directed as reflux to the feed side, wherein for both of the phases the flow apportioned to the product side versus the feed side is controlled. There is no functional requirement for the reflux outlets from internal decanter 30 to have any particular orientation relative to the feed side or product side of the dividing wall.

A sixth embodiment of the invention is a system for controlling the reflux flows in a dividing wall column 10, comprising a dividing wall 20 having a feed side 14 and a product side 16, a decanter 30 with optional collector tray 42, a liquid-liquid phase interface level controller 45, a liquid level controller 49, a first flow controller 56 with associated control valve, a second flow controller 46 with associated flow control valve, a third flow controller 50 with associated flow control valve, a fourth flow controller 39 with associated control valve, a first ratio controller 31, and a second ratio controller 41. There is no functional requirement for the reflux outlets from internal decanter 30 to have any particular orientation relative to the feed side or product side of the dividing wall.

For feed composition and product requirements such that the composition of combined vapor 28 from the feed and product sides of the dividing wall can meet the requirements for net overhead vapor product 15 and net overhead liquid product 23 without any upper-section active distillation tray(s) 25, then active distillation tray(s) 25 can be deleted from the design. In that case, the function of internal decanter 30 can be performed by changing the design of receiver 19 to a three-phase receiver similar to settler 51.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

While the invention has been described with what are presently considered the preferred embodiments, it is to be understood that the invention is not limited to the disclosed embodiments, but it is intended to cover various modifications and equivalent arrangements included within the scope of the appended claims.

Specific Embodiments

While the following is described in conjunction with specific embodiments, it will be understood that this description is intended to illustrate and not limit the scope of the preceding description and the appended claims.

A first embodiment of the invention is a process, comprising feeding crude phenol to a dividing wall column, the dividing wall column having a dividing wall forming a feed side and a product side, the crude phenol being fed to the feed side at a point lower than a top of the dividing wall and above a bottom of the dividing wall; collecting the liquid reflux from the column above the dividing wall, the liquid reflux forming an aqueous phase and an organic phase; separating the liquid reflux into two streams above the dividing wall, a first stream comprising primarily the aqueous phase and a second stream comprising primarily the organic phase; passing at least a portion of the first stream to the product side of the dividing wall column at a point lower than the top of the dividing wall and above a bottom of the dividing wall; dividing the second stream into a first portion and a second portion; passing the first portion of the second stream to the feed side of the dividing wall column at a point lower than the top of the dividing wall and above the point where the crude phenol is fed; passing the second portion of the second stream to the product side of the dividing wall column at a point lower than the top of the dividing wall and above the bottom of the dividing wall; and removing a liquid sidecut stream from an outlet on the product side of the dividing wall column at a point lower than where the first stream and the second portion of the second stream are introduced and above a bottom of the dividing wall, the liquid sidecut stream forming two phases. An embodiment of the invention is one, any or all of prior embodiments in this paragraph up through the first embodiment in this paragraph further comprising controlling a flow rate of the first stream, a flow rate of the first portion of the second stream, and a flow rate of the second portion of the second stream to maintain a desired flow rate to the feed side of the dividing wall column and a desired flow rate to the product side of the dividing wall column. An embodiment of the invention is one, any or all of prior embodiments in this paragraph up through the first embodiment in this paragraph wherein passing the first stream to the product side of the dividing wall column comprises passing all of the first stream to the product side of the dividing wall column. An embodiment of the invention is one, any or all of prior embodiments in this paragraph up through the first embodiment in this paragraph wherein passing at least the portion of the first stream to the product side of the dividing wall column comprises; dividing the first stream into a first portion and a second portion; wherein passing at least a portion of the first stream to the product side comprises passing the first portion of the first stream to the product side of the dividing wall column; and passing the second portion of the first stream to the feed side of the dividing wall column at a point lower than the top of the dividing wall and above the point where the crude phenol is fed. An embodiment of the invention is one, any or all of prior embodiments in this paragraph up through the first embodiment in this paragraph further comprising controlling a flow rate of the first portion of the first stream, a flow rate of the second portion of the first stream, a flow rate of the first portion of the second stream, and a flow rate of the second portion of the second stream to maintain a desired flow to the feed side of the dividing wall column and a desired flow rate to the product side of the dividing wall column. An embodiment of the invention is one, any or all of prior embodiments in this paragraph up through the first embodiment in this paragraph further comprising separating the liquid sidecut stream into a higher density stream having a first density and a lower density stream having a second density less than the first density. An embodiment of the invention is one, any or all of prior embodiments in this paragraph up through the first embodiment in this paragraph wherein separating the liquid sidecut stream into the higher density stream and the lower density stream comprises separating the liquid sidecut stream into the higher density stream and the lower density stream in a settler. An embodiment of the invention is one, any or all of prior embodiments in this paragraph up through the first embodiment in this paragraph wherein separating the liquid reflux into two streams comprises separating the liquid reflux into two streams using an internal decanter. An embodiment of the invention is one, any or all of prior embodiments in this paragraph up through the first embodiment in this paragraph further comprising cooling the liquid sidecut stream before separating the liquid sidecut stream. An embodiment of the invention is one, any or all of prior embodiments in this paragraph up through the first embodiment in this paragraph further comprising at least one of: sensing at least one parameter of the process and generating a signal or data from the sensing; generating and transmitting a signal; or generating and transmitting data.

A second embodiment of the invention is an apparatus, comprising a dividing wall column having a dividing wall forming a feed side and a product side, the dividing wall column having a separator positioned above the dividing wall of the dividing wall column, an aqueous reflux outlet above the dividing wall and an organic reflux outlet above the dividing wall, the feed side having a feed inlet below a top of the dividing wall and above the bottom of the dividing wall, a feed side reflux inlet below a top of the dividing wall and above the feed inlet in fluid communication with the second reflux outlet, and the product side having a product outlet below a top of the dividing wall and above the bottom of the dividing wall, and a product side reflux inlet below the top of the dividing wall and above the product outlet in fluid communication with the first reflux outlet and the second reflux inlet. An embodiment of the invention is one, any or all of prior embodiments in this paragraph up through the second embodiment in this paragraph, wherein the separator comprises a decanter. An embodiment of the invention is one, any or all of prior embodiments in this paragraph up through the second embodiment in this paragraph, wherein the feed side reflux inlet is in fluid communication with the first reflux outlet. An embodiment of the invention is one, any or all of prior embodiments in this paragraph up through the second embodiment in this paragraph, further comprising at least one flow meter on the product side of the dividing wall column to maintain a desired ratio of liquid. An embodiment of the invention is one, any or all of prior embodiments in this paragraph up through the second embodiment in this paragraph, further comprising at least one flow meter on the feed side of the dividing wall column to maintain a desired ratio of liquid.

An embodiment of the invention is one, any or all of prior embodiments in this paragraph up through the second embodiment in this paragraph, wherein the aqueous reflux outlet is positioned at or above the separator. An embodiment of the invention is one, any or all of prior embodiments in this paragraph up through the second embodiment in this paragraph, wherein the organic reflux outlet is positioned at or above the aqueous reflux outlet. An embodiment of the invention is one, any or all of prior embodiments in this paragraph up through the second embodiment in this paragraph further comprising a settler in fluid communication with the product outlet, the settler having an inlet and at least two outlets.

A third embodiment of the invention is a process, comprising feeding crude phenol to a dividing wall column, the dividing wall column having a dividing wall forming a feed side and a product side, the crude phenol being fed to the feed side at a point lower than a top of the dividing wall and above a bottom of the dividing wall; collecting the liquid reflux from the column above the dividing wall, the liquid reflux forming an aqueous phase and an organic phase; separating the liquid reflux into two streams above the dividing wall, a first stream comprising primarily the aqueous phase and a second stream comprising primarily the organic phase; passing at least a portion of the first stream to the product side of the dividing wall column at a point lower than the top of the dividing wall and above a bottom of the dividing wall; dividing the second stream into a first portion and a second portion; passing the first portion of the second stream to the feed side of the dividing wall column at a point lower than the top of the dividing wall and above the point where the crude phenol is fed; passing the second portion of the second stream to the product side of the dividing wall column at a point lower than the top of the dividing wall and above the bottom of the dividing wall; controlling a flow rate of the first stream, a flow rate of the first portion of the second stream, and a flow rate of the second portion of the second stream to maintain a desired flow to the feed side of the dividing wall column and a desired flow rate to the product side of the dividing wall column; removing a liquid sidecut stream from an outlet on the product side of the dividing wall column at a point lower than where the first stream and the second portion of the second stream are introduced and above a bottom of the dividing wall, the liquid sidecut stream forming two phases; and separating the liquid sidecut stream into a higher density stream having a first density and a lower density stream having a second density less than the first density. An embodiment of the invention is one, any or all of prior embodiments in this paragraph up through the third embodiment in this paragraph wherein passing at least the portion of the first stream to the product side of the dividing wall column comprises; dividing the first stream into a first portion and a second portion; wherein passing at least a portion of the first stream to the product side comprises passing the first portion of the first stream to the product side of the dividing wall column; passing the second portion of the first stream to the feed side of the dividing wall column at a point lower than the top of the dividing wall and above the point where the crude phenol is fed; and controlling a flow rate of the first portion of the first stream, and a flow rate of the second portion of the first stream to maintain a desired flow to the feed side of the dividing wall column and a desired flow rate to the product side of the dividing wall column.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A fractionation process, comprising:
   feeding crude phenol to a dividing wall column, the dividing wall column having a dividing wall forming a feed side and a product side, the crude phenol being fed to the feed side at a point lower than a top of the dividing wall and above a bottom of the dividing wall;
   collecting liquid reflux from a tray above the dividing wall, the liquid reflux forming an aqueous phase and an organic phase, wherein the liquid reflux is at least a portion of condensed vapor from the column;
   separating the liquid reflux into two streams above the dividing wall, a first stream comprising primarily the aqueous phase and a second stream comprising primarily the organic phase;
   passing at least a portion of the first stream to the product side of the dividing wall column at a point lower than the top of the dividing wall and above a bottom of the dividing wall;
   dividing the second stream into a first portion and a second portion;
   passing the first portion of the second stream to the feed side of the dividing wall column at a point lower than the top of the dividing wall and above the point where the crude phenol is fed;
   passing the second portion of the second stream to the product side of the dividing wall column at a point lower than the top of the dividing wall and above the bottom of the dividing wall; and
   removing a liquid sidecut stream from an outlet on the product side of the dividing wall column at a point lower than where the first stream and the second portion of the second stream are introduced and above a bottom of the dividing wall, the liquid sidecut stream forming two phases.

2. The process of claim 1 further comprising:
   controlling a flow rate of the first stream, a flow rate of the first portion of the second stream, and a flow rate of the second portion of the second stream to maintain a desired flow rate to the feed side of the dividing wall column and a desired flow rate to the product side of the dividing wall column.

3. The process of claim 1 wherein passing the first stream to the product side of the dividing wall column comprises passing all of the first stream to the product side of the dividing wall column.

4. The process of claim 1 wherein passing at least the portion of the first stream to the product side of the dividing wall column comprises;
   dividing the first stream into a first portion and a second portion;
   wherein passing at least a portion of the first stream to the product side comprises passing the first portion of the first stream to the product side of the dividing wall column; and
   passing the second portion of the first stream to the feed side of the dividing wall column at a point lower than the top of the dividing wall and above the point where the crude phenol is fed.

5. The process of claim 4 further comprising:
   controlling a flow rate of the first portion of the first stream, a flow rate of the second portion of the first stream, a flow rate of the first portion of the second stream, and a flow rate of the second portion of the second stream to maintain a desired flow to the feed side of the dividing wall column and a desired flow rate to the product side of the dividing wall column.

6. The process of claim 1 further comprising:
   separating the liquid sidecut stream into a higher density stream having a first density and a lower density stream having a second density less than the first density.

7. The process of claim 6 wherein separating the liquid sidecut stream into the higher density stream and the lower density stream comprises separating the liquid sidecut stream into the higher density stream and the lower density stream in a settler.

8. The process of claim 1 wherein separating the liquid reflux into two streams comprises separating the liquid reflux into two streams using an internal decanter.

9. The process of claim 1 further comprising:
   cooling the liquid sidecut stream before separating the liquid sidecut stream.

10. A fractionation process, comprising:
    feeding crude phenol to a dividing wall column, the dividing wall column having a dividing wall forming a feed side and a product side, the crude phenol being fed to the feed side at a point lower than a top of the dividing wall and above a bottom of the dividing wall;
    collecting liquid reflux from a tray above the dividing wall, the liquid reflux forming an aqueous phase and an organic phase, wherein the liquid reflux is at least a portion of condensed vapor from the column;
    separating the liquid reflux into two streams above the dividing wall, a first stream comprising primarily the aqueous phase and a second stream comprising primarily the organic phase;
    passing at least a portion of the first stream to the product side of the dividing wall column at a point lower than the top of the dividing wall and above a bottom of the dividing wall;
    dividing the second stream into a first portion and a second portion;

passing the first portion of the second stream to the feed side of the dividing wall column at a point lower than the top of the dividing wall and above the point where the crude phenol is fed;

passing the second portion of the second stream to the product side of the dividing wall column at a point lower than the top of the dividing wall and above the bottom of the dividing wall;

controlling a flow rate of the first stream, a flow rate of the first portion of the second stream, and a flow rate of the second portion of the second stream to maintain a desired flow rate to the feed side of the dividing wall column and a desired flow rate to the product side of the dividing wall column;

removing a liquid sidecut stream from an outlet on the product side of the dividing wall column at a point lower than where the first stream and the second portion of the second stream are introduced and above a bottom of the dividing wall, the liquid sidecut stream forming two phases; and separating the liquid sidecut stream into a higher density stream having a first density and a lower density stream having a second density less than the first density.

11. The process of claim 1 wherein passing at least the portion of the first stream to the product side of the dividing wall column comprises;

dividing the first stream into a first portion and a second portion;

wherein passing at least a portion of the first stream to the product side comprises passing the first portion of the first stream to the product side of the dividing wall column;

passing the second portion of the first stream to the feed side of the dividing wall column at a point lower than the top of the dividing wall and above the point where the crude phenol is fed; and controlling a flow rate of the first portion of the first stream, and a flow rate of the second portion of the first stream to maintain a desired flow rate to the feed side of the dividing wall column and a desired flow rate to the product side of the dividing wall column.

12. The process of claim 1 further comprising at least one of:

sensing at least one parameter of the process and generating a signal or data from the sensing;

generating and transmitting a signal; or generating and transmitting data.

* * * * *